United States Patent [19]
Horgan

[11] Patent Number: 5,645,532
[45] Date of Patent: Jul. 8, 1997

[54] RADIOPAQUE CUFF PERITONEAL DIALYSIS CATHETER

[75] Inventor: Donna Horgan, Berkley, Mass.

[73] Assignee: Sil-Med Corporation, Taunton, Mass.

[21] Appl. No.: 610,526

[22] Filed: Mar. 4, 1996

[51] Int. Cl.$^6$ .................................................. A61F 2/00
[52] U.S. Cl. .................................... 604/117; 623/1
[58] Field of Search ................. 64/286, 117; 623/1, 623/11

[56] References Cited

U.S. PATENT DOCUMENTS 5,047,050  9/1991  Arpesani ..................... 623/1

Primary Examiner—Sam Rimell
Attorney, Agent, or Firm—John M. Brandt

[57] ABSTRACT

Peritoneal dialysis catheter cuffs positioned at one or both ends of the body implantation tunnel to secure the catheter in position and to seal the entrance site against infection are rendered radiopaque by a variety of means to identify the position of the cuffs during and after the catheter implantation procedure. The cuffs may alternatively be adhered to the catheter by an adhesive having a radiopaque material included as an integral constituent thereof, may be mounted coaxially with a band of radiopaque material or may be formed of a fabric having radiopaque material as an integral part thereof.

3 Claims, 1 Drawing Sheet

RADIOPAQUE CUFF PERITONEAL DIALYSIS CATHETER

BACKGROUND OF THE INVENTION

1. Field of the Invention

The invention resides in the field of body implantable peritoneal dialysis catheters and more particularly relates to subcutanious sealing cuffs employed therewith.

2. Description of the Prior Art

Peritoneal catheters are body implantable devices used in the practice of peritoneal dialysis as a method of blood cleansing in renal failure patients. The catheters pass through the body and terminate in the peritoneum allowing the introduction and withdrawal of a dialysate required by the process.

Most such catheters have at least one and often two fibrous cuffs which surround and are attached to the catheter in the subcutaneous region and function to integrate with the body to inhibit infection and prevent fluid leakage.

As these catheters remain in the body over a prolonged period of time, they are subject to stress and strain from body motion which may result in some displacement in position which cannot be immediatley observed or detected. Further, there is a need to know as exactly as possible the position of the cuffs during the implantation procedure to properly locate the catheter to prevent future problems, particularly infection at the entrance incession.

Rendering portions of peritoneal dialysis catheters radiopaque has been suggested in the prior art. For example, U.S. Pat. No. 4,392,855 Oreopoulos et al discloses the concept of placiang a radiopaque strip on the catheter itself as well as on discs and a bead associated therewith. However, to the best of the inventor's knowledge the concept of rendering radiopaque the most important portion of the catheter from the standpoint of implantation has not been addressed.

SUMMARY OF THE INVENTION

The invention may be summarized as an improvement in peritoneal dialysis catheters wherein fibrous cuffs located on either or both ends of the subcutaneous portion of the catheter are rendered radiopaque to provide their precise location during and after implantation by X-ray imaging.

This may be accomplished in a variety of ways including providing a radiopaque material as an integral constituent of the adhesive which is used to bond the cuffs to the catheter outer wall; placing a thin band of radiopaque material between the cuff and the catheter outer wall; and including radiopaque material as an integral part of the fabric which the cuffs are manufactured of.

The disruption of the preferred embodiment and drawings which follow more specifically detail the invention disclosed above.

DESCRIPTION OF THE PREFERRED EMBODIMENT

Figure 1:
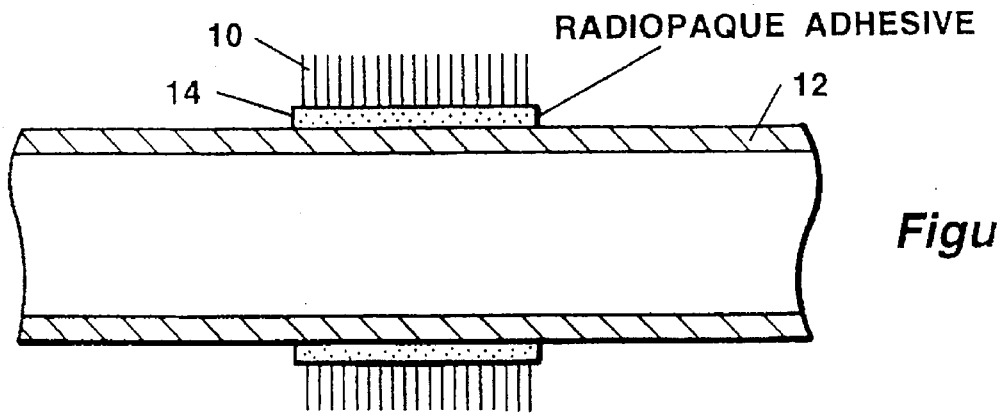
FIG. 1 is a cross sectional schematic drawing of the preferred embodiment of the invention.

Referring first to FIG. 1 there is shown a cross sectional view of the preferred embodiment of the invention wherein a prior art cuff 10 attached to a silicon rubber catheter 12 is rendered radiopaque utilizing an adhesive 14 having a radiopaque material as an integral constituent thereof. The cuff may be comprised of medical grade DACRON obtainable from Meadox Medicals, Inc. of Oakland, N.J., and bonded to the catheter by a suitable adhesive for example SWS-951, a silicon adhesive obtainable from Perma-Flex Mold Co. of Columbus, Ohio, to which has been added powdered barium sulfate.

It has been found that as little as one percent by weight of barium sulfate added to the adhesive will produce a visible cuff by X-ray imaging and that the images improve by additional additive up to about three percent. Pull tests of samples bonded with adhesive with from one to twenty percent of additive showed no deterioration in the bonding strength over the entire range as compared to cuffs bonded with adhesive alone without the radiopaque material.

Figure 2:
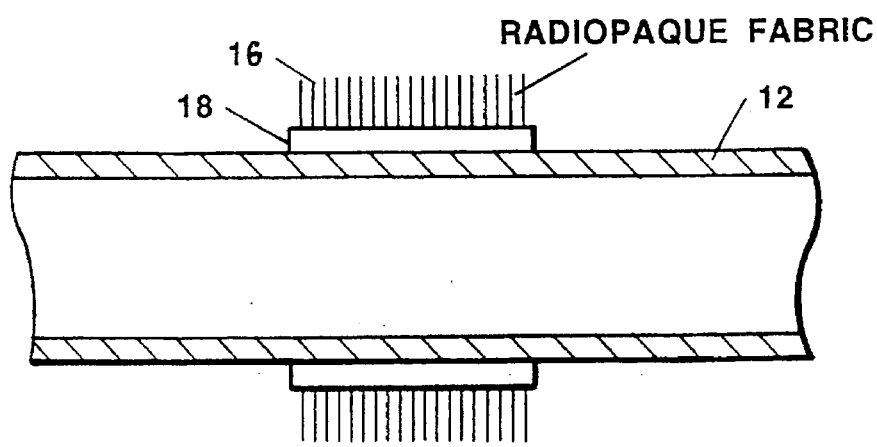
FIG. 2 is a cross sectional drawing of an alternative embodiment of the invention.

FIG. 2 illustrates an alternative embodiment of the invention wherein the cuff fabric 16 itself is rendered radiopaque by the inclusion of an appropriate material such as a barium compound in the basic material from which the fabric is manufactured and bonded with a non-radiopaque adhesive 18.

Figure 3:
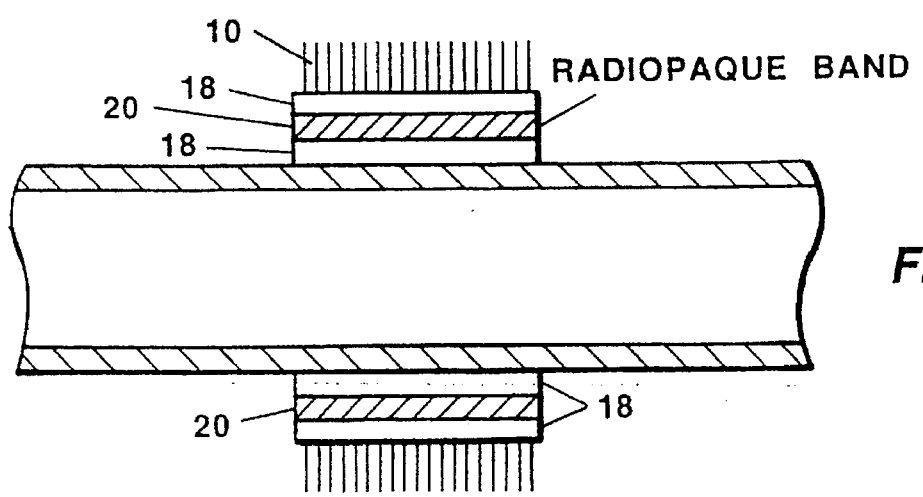
FIG. 3 is an additional alternative embodiment of the invention.

Finally, FIG. 3 shows an additional alternative embodiment in which a band 20 of radiopaque material, for example, silicon rubber into which an appropriate barium compound has been added, is interposed between the cuff and the catheter and bonded to each by a suitable non-radiopaque adhesive such as the aforementioned SWS951.

As other embodiments may become obvious from the disclosure above the invention is accordingly defined by the following claims.

What is claimed is:

1. In a peritoneal catheter adapted for implantation in the human body having a distal end arranged to reside in the peritoneal cavity, a proximal end arranged to reside external to the body, and a subcutaneous section between said distal and proximal ends, the improvement which compises:

at least one radiopaque fibrous cuff positioned at, surrounding, and attached to said subcutaneous section, said cuff adapted to integrate with body tissue to seal said catheter upon said implantation, said cuff observable by X-ray imaging techniques, said radiopaque cuff comprising an outer band of fibrous material and an inner band of radiopaque material said inner and outer bands attached by an adhesive and said inner band and said subcutaneous section attached by an adhesive.

2. In a peritoneal catheter adaptd for implantation in the human body having a distal end arranged to reside in the peritoneal cavity, a proximal end arranged to reside external to the body, and a subcutaneous section between said distal and proximal ends, the improvement which comprises:

at least one radiopaque fibrous cuff positioned at, surrounding, and attached to said subcutaneous section, said cuff adapted to integrate with body tissue to seal said catheter upon said implantation, said cuff observable by X-ray imaging techniques, said radiopaque cuff comprising a band of fibrous material attached to said subcutaneous section by an adhesive having radiopaque material as an integral constituent thereof.

3. The apparatus of claim 2 wherein said adhesive comprises a silicon adhesive having barium sulfate in the amount of one to twenty percent by weight added thereto.

* * * * *